(12) United States Patent
Bedard et al.

(10) Patent No.: US 7,623,988 B2
(45) Date of Patent: Nov. 24, 2009

(54) METHOD AND APPARATUS FOR THE MONITORING OF CLINICAL STATES

(75) Inventors: Michel Bedard, Saint-Augustin-de-Desmaures (CA); Dany Nolet, Ancienne-Lorette (CA)

(73) Assignee: Cybiocare Inc., Sainte-Foy (CA)

( * ) Notice: Subject to any disclaimer, the term of this patent is extended or adjusted under 35 U.S.C. 154(b) by 756 days.

(21) Appl. No.: 11/165,003

(22) Filed: Jun. 23, 2005

(65) Prior Publication Data

US 2006/0004270 A1      Jan. 5, 2006

Related U.S. Application Data

(60) Provisional application No. 60/581,727, filed on Jun. 23, 2004.

(51) Int. Cl.
G06F 15/00 (2006.01)
A61B 5/00 (2006.01)
(52) U.S. Cl. ........................ 702/189; 600/316
(58) Field of Classification Search ................. 702/182, 702/189; 600/310, 316, 317; 435/14
See application file for complete search history.

(56) References Cited

U.S. PATENT DOCUMENTS

| | | | |
|---|---|---|---|
| 4,365,637 A | 12/1982 | Johnson | |
| 4,509,531 A | 4/1985 | Ward | |
| 4,783,366 A | 11/1988 | Shimogo et al. | |
| 5,551,422 A | 9/1996 | Simonsen et al. | |
| 5,676,143 A | 10/1997 | Simonsen et al. | |
| 5,782,755 A | 7/1998 | Chance et al. | |
| 6,066,847 A | 5/2000 | Rosenthal | |
| 6,067,463 A | 5/2000 | Jeng et al. | |
| 6,151,517 A | 11/2000 | Honigs et al. | |
| 2003/0191377 A1* | 10/2003 | Robinson et al. | 600/310 |
| 2004/0024553 A1* | 2/2004 | Monfre et al. | 702/104 |

* cited by examiner

*Primary Examiner*—Bryan Bui
(74) *Attorney, Agent, or Firm*—Timothy Keefer; Polsinelli Shughart PC

(57) ABSTRACT

A method and apparatus to monitor clinical states, for example hypoglycaemia, hyperglycaemia or an ischemic state, and to detect if a user if affected by such a state. In one embodiment, the method and apparatus use a correlation between one or more non-invasive physical measurements of the body of the subject and a reference value of blood-glucose of the subject to compute an estimation parameter value, and comparing that estimation parameter value with a critical parameter value indicative of the presence of a clinical state, for example hypoglycaemia, hyperglycaemia. In another embodiment, the algorithm estimates chromophore concentrations and the scattering coefficient in order to compute a level of oxygen saturation and detect the presence of an ischemic state.

30 Claims, 7 Drawing Sheets

METHOD AND APPARATUS FOR THE MONITORING OF CLINICAL STATES

CROSS-REFERENCE TO RELATED APPLICATION

This application claims the benefits of U.S. provisional patent applications No. 60/581,727 filed Jun. 23, 2004; which is hereby incorporated by reference.

TECHNICAL FIELD

The present invention relates to a method and apparatus for the monitoring of clinical states. The present invention further relates to a method and apparatus for the estimation of chromophore concentrations and scattering coefficient.

BACKGROUND

Hypoglycemia is an important glucose related complication of diabetes. A common blood glucose monitoring method is an invasive method which periodically measures the blood glucose of a patient by obtaining a blood sample from an individual by a variety of methods, such as by needle or lance. The individual inserts a plastic strip carrying chemistry into a blood glucose meter and then applies a blood sample onto the strip for the measurement of blood glucose concentration by determination of change in reflectance or electric signal of a biosensor. This method produces measurements that, while very accurate, are too infrequent to detect hypoglycemic episodes. Frequently, in order to avoid hypoglycemia, diabetics maintain abnormally high blood glucose levels to prevent low blood glucose levels in between blood glucose measurements. This constant high blood glucose level often causes long-term complications, namely, retinopathy, neuropathy, nephropathy, and cardiovascular disease. In effect, the present blood glucose monitoring methods are forcing many diabetics to pay for a lower rate of acute complications with a higher rate of chronic complications later in life.

Thus, the most important factor for reducing diabetes-associated complications is the maintenance of an appropriate level of blood glucose. The maintenance of the appropriate level of blood glucose may prevent and even reverse many of the effects of diabetes.

Recently, new non-invasive approaches of measuring the level of blood glucose have been pursued. For example, U.S. Pat. No. 4,509,531 discloses a physiological monitor that continuously monitors changes in galvanic skin resistance and/or temperature of the wearer in order to detect the onset of a hypoglycaemic state. Similarly U.S. Pat. No. 4,365,637 discloses a device that senses the buildup of perspiration on the skin of the wearer in order to detect the onset of insulin shock. The main problem with these approaches is that they monitor symptoms of hypoglycaemia or insulin shock and are not necessarily correlated with the level blood glucose. Thus, these approaches are not suited for commercial use as they generate an unacceptable level of false alarms.

U.S. Pat. No. 5,676,143 and U.S. Pat. No. 5,551,422 disclose a method and apparatus for analytical determination of glucose in a biological matrix by measuring the relative intensity of scattered light in a tissue boundary and deriving a blood glucose concentration value. The main problem with this approach is long term drift errors in the estimation of blood glucose values because the initial calibration is not specific to the individual wearing the device and there is no periodic recalibration using an external reference blood glucose meter. Thus it is subject to many interfering parameters that may affect the measurement with time.

U.S. Pat. No. 6,882,940 discloses methods and devices for prediction of hypoglycemic events by obtaining a series of glucose measurement values, performed using a near-IR spectrometer, and skin conductance and/or temperature values. Once again, the main problem with this approach is long term drift errors in the estimation of blood glucose values because the initial calibration is not specific to the individual wearing the device and there is no periodic recalibration using an external reference blood glucose meter. Thus it is subject to many interfering parameters that may affect the measurement with time.

U.S. Pat. No. 6,066,847 discloses a procedure for verifying the accuracy of a non-invasive blood glucose measurement instrument by electrically connecting the instrument to a reference blood glucose meter. In the case there is too much discrepancy between the two measurements, the procedure prevents the individual from continuing to use the non-invasive blood glucose measurement instrument. The problem with such an approach is that once a discrepancy has been detected the non-invasive blood glucose measurement instrument is no longer usable until it is recalibrated.

SUMMARY

The present invention relates to a method for detecting a clinical state in a subject, comprising acquiring a reference value of blood-glucose of the subject, correlating one or more non-invasive physical measurements of the body of the subject with the reference value of blood-glucose of the subject, measuring the one or more non-invasive physical measurements of the body of the subject, computing an estimation parameter value representative of a variation in glucose value using the measured one or more non-invasive physical measurements and the correlation between the one or more non-invasive physical measurements of the body of the subject with the reference value of blood-glucose of the subject, comparing the estimation parameter value with a critical parameter value, wherein the critical parameter value is indicative of a clinical state, and indicating that a clinical state is detected if the estimation parameter value has reached the critical parameter value.

The present invention further relates to the above mentioned method for detecting a clinical state in a subject wherein the one or more non-invasive physical measurements of the body of the subject is the reflectance of light in the skin of the subject and wherein measuring the one or more non-invasive physical measurements of the body of the subject includes propagating at least one probing light beam into the skin of the subject and measuring reflectance values of the at least one probing light beam from at least two distances from the propagation point.

Furthermore, the present invention relates to a method for detecting a clinical state in a subject, comprising acquiring a reference value of blood-glucose of the subject, correlating at least two parameters of skin of the body of the subject with the reference value of blood-glucose of the subject, propagating at least two probing light beams into the skin from at least one propagation point, measuring reflectance values of the at least two probing light beams from at least two distances from the at least one propagation point, estimating values representative of the at least two parameters of skin of the body of the subject using the measured reflectance values and a mathematical skin parameter estimation model, computing an estimation parameter value representative of a variation in glucose value using the estimated values of the at least two parameters of skin of the body of the subject and the correlation between the at least two parameters of skin of the body of the subject with the reference value of blood-glucose of the subject, comparing the estimation parameter value with a critical parameter value, wherein the critical parameter value is indicative of a clinical state and indicating that a clinical state is detected if the estimation parameter value has reached the critical parameter value.

The present invention also relates to a method for computing an estimate of a value representative of at least one parameter of skin selected from a group including chromophore concentrations and a scattering coefficient, comprising, propagating at least two probing light beams into the skin from at least one propagation point, measuring reflectance values of the at least two probing light beams from at least two distances from the at least one propagation point, computing estimates of the at least one parameter of skin of the body of the subject using a reflectance mathematical model and outputting the estimate of the value representative of the at least one selected parameters of skin.

As well, the present invention relates to an apparatus implementing the above mentioned methods.

BRIEF DESCRIPTION OF THE FIGURES

A non-limitative embodiment of the invention will now be described by way of example only with reference to the accompanying drawings, in which.

DETAILED DESCRIPTION

Generally stated, an apparatus according to an embodiment of the present invention monitors glucose related clinical states, for example hypoglycaemia, hyperglycaemia or ischemic state, and detects if a user if affected by such a state. The apparatus may also be used to estimate the concentration of chromophores and the scattering coefficient. In order detect a glucose related clinical state, estimate the concentration of chromophores or estimate the scattering coefficient, the apparatus generates a probing light beam and analyses the back scattered light, as will be described hereinbelow.

Figure 1:
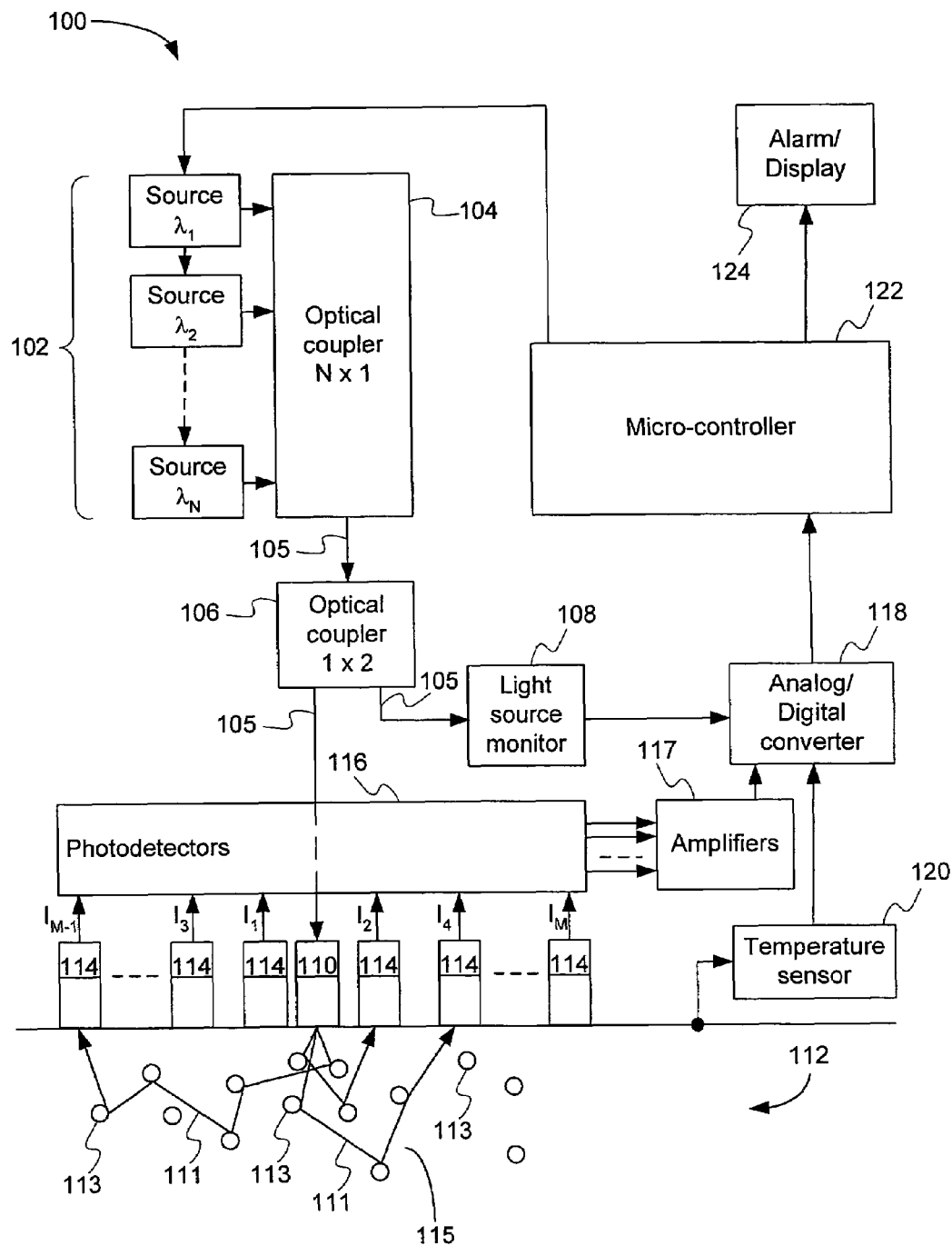
FIG. 1 is a block diagram showing an apparatus for the monitoring of glucose related clinical states and estimation of chromophore concentrations and scattering coefficient, according to a non-limitative embodiment of the present invention.

Referring to FIG. 1, the monitoring apparatus 100 uses N light sources (or emitters) 102, each generating a probing light at respective predetermined wavelengths $\lambda_1$ to $\lambda_N$, coupled to a N×1 optical coupler 104 in order to generate a probing light beam 105 comprising all of the N wavelengths of the N individual light sources 102. The number of light sources 102, and thus wavelengths, as well as their power levels, may vary depending on the application.

The probing light beam 105 then goes through a 1×2 optical coupler 106 that provides the probing light beam 105 to both a light source monitor 108 and to an emitter collimating optic 110. The emitter collimating optic 110, preferably in direct contact with the skin, propagates the probing light beam 105 into the dermis 112 of the skin. The probing light beam 105 is then attenuated and scattered into a number of reflected beams 111 by various scatterers 113 and chromophores 115, which are present in the dermis. The attenuated and reflected beams 111 are then received by receiver collimating optics 114, providing optical signals $I_1$ to $I_M$ to photodetectors 116. Each of the receiver collimating optics 114 is positioned at a distance away from the emitter collimating optic 110 that is different from that of the other receiver collimating optics 114. The number of receiver collimating optics 114 may vary according to the application. A temperature sensor 120 provides a signal indicative of the temperature of the skin.

At least one Analog to Digital Converter (ADC) 118 then converts the analog signals from the light source monitor 108, the photodetectors 116, as amplified by amplifiers 117, and the temperature sensor 120 into digital signals which are provided to a micro-controller 122. The micro-controller 122 includes an algorithm that controls the operations of the apparatus and performs the monitoring of certain clinical states, and may also perform estimations of certain biological parameters such as, for example, chromophore concentrations and scattering coefficient, which will be further described below. The results of the monitoring and estimations are then given to the wearer of the monitoring apparatus 100 by either setting a visual, audio and/or mechanical alarm, when a certain clinical state is detected, of displaying the result via alarm/display 124. The micro-controller 122 is also connected to an input/output 126 through which data such as, for example, a reference blood glucose level may be provided to the monitoring apparatus 100 or through which data such as, for example, chromophore concentrations and scattering coefficient may be provided from the monitoring apparatus 100 to other devices. It is to be understood that the input/output 126 may be any type of interface such as, for example, an electrical, infrared (IR) or a radio frequency (RF) interface.

In an alternate embodiment, the N×1 optical coupler 104 and the 1×2 optical coupler 106 may be replaced by a single N×2 coupler or they may be omitted altogether, the N light sources 102 being independently propagated into the dermis 112, and one, or more, of the receiver collimating optics 114 may be used to replace the light source monitor 108.

As mentioned previously, the micro-controller 122 includes an algorithm that controls the operations of the apparatus and is also configured so as to monitor glucose related clinical states, for example hypoglycaemia and hyperglycaemia, or other clinical states, for example an ischemic state, and detects if a user if affected by such a state. The general monitoring and detection algorithm is depicted by the flow chart shown in FIG. 2. The steps composing the algorithm are indicated by blocks 232 to 242.

At block 232, the algorithm starts by receiving, as an input, a reference glucose value $g_{ref}$ provided by, for example, a reference meter such as a conventional blood-glucose monitor. Then, at block 234, one or more non-invasive physical measurements of the body are correlated with the reference glucose value $g_{ref}$ using a predetermined relation.

At block 236, the algorithm measures the non-invasive physical measurements selected at block 234 on the body of the user and then determines, at block 238, if a clinical state exists by verifying if the non-invasive physical measurements taken at block 238 have reached a critical threshold value using the correlation relation. If a clinical state is determined then, at block 242, the algorithm generates an alarm and/or displays the determined clinical state. If not, the algorithm goes to block 240 where it verifies if a new reference glucose value is available, if yes it proceeds to block 232 where the new reference glucose value is inputted, if not, it then proceeds back to block 236 for the next iteration.

It is to be understood that for better performances, a new reference glucose value should be inputted at either periodic time intervals or a certain number of times per given period of use.

EXAMPLES

Figure 2:
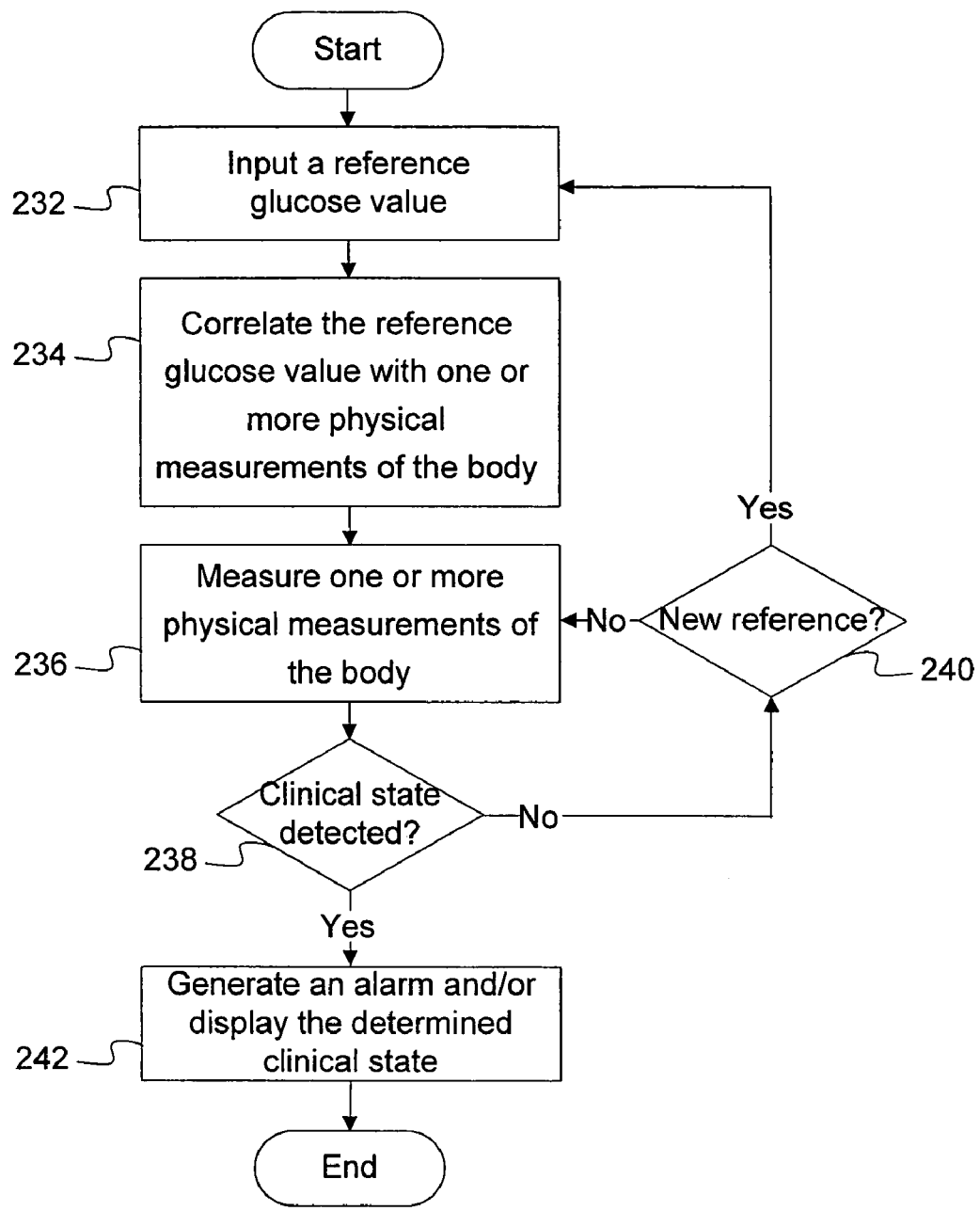
FIG. 2 is a flow diagram of a general algorithm for the monitoring of glucose related clinical states, according to a non-limitative embodiment of the present invention.
Figure 3:
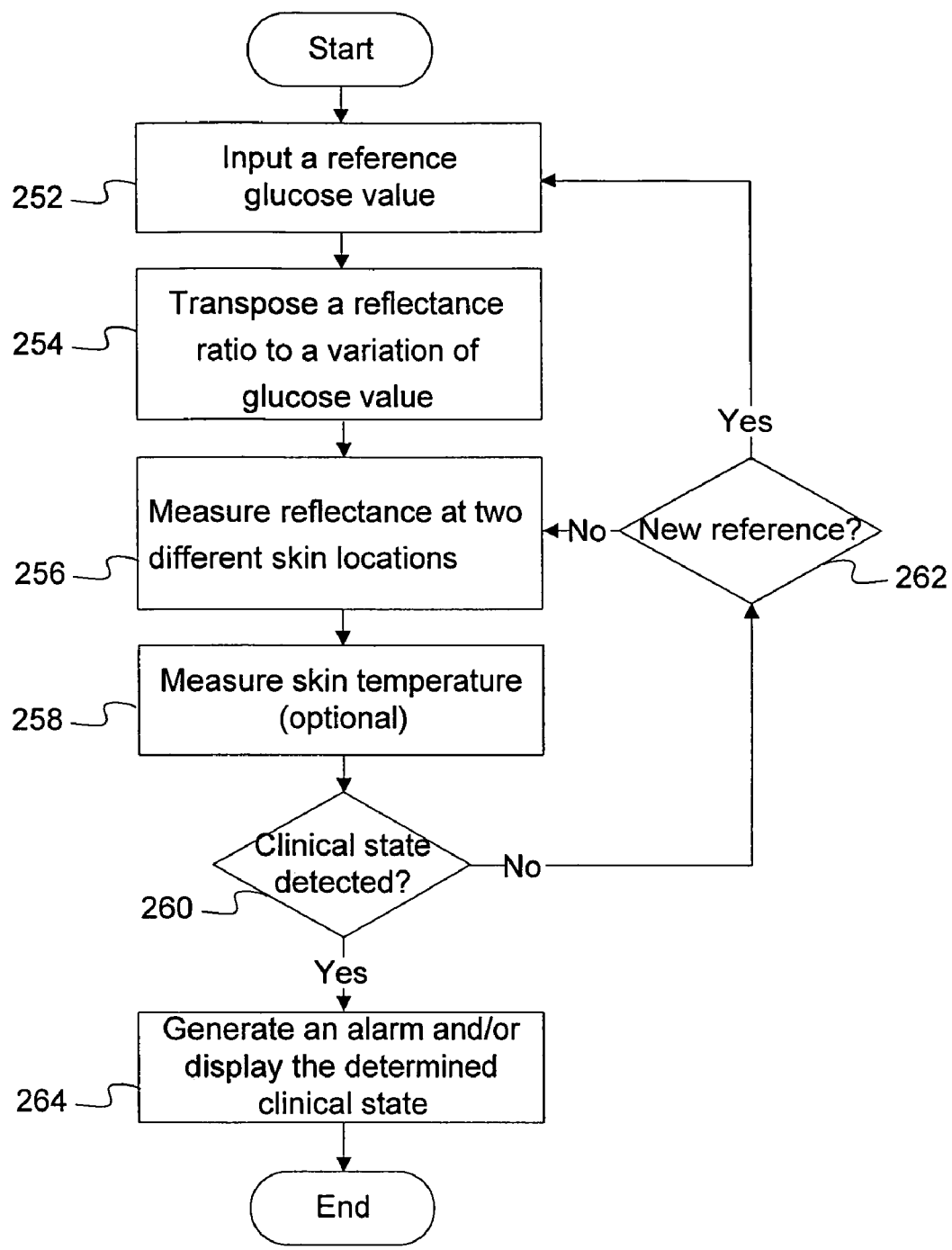
FIG. 3 is a flow diagram of a first example of a specific embodiment of the algorithm illustrated in FIG. 2.

A first example of a specific embodiment of the general monitoring and detection algorithm illustrated in FIG. 2 is depicted by the flow chart shown in FIG. 3. The steps composing the algorithm are indicated by blocks 252 to 264.

At block 252, the algorithm starts by receiving, as an input, a reference glucose value $g_{ref}$ provided by, for example, a reference meter such as a conventional blood-glucose monitor. Then, at block 254, the algorithm transposes a reflectance ratio into a variation of glucose value using a predetermined relation, for example:

$$\Delta g = C_{cal} \cdot \text{Ratio}_{ref_t} \qquad \text{Equation 1}$$

where $\Delta g$ is the variation in glucose value;

$C_{cal}$ is a calibration constant providing a best fit between the variation in glucose and the variation of the reflectance ratio;

$$\text{Ratio}_{ref_t} = \left[ \frac{\left[\left(\frac{\overrightarrow{R_{mes}^{(2)}}}{R_{mes}^{(1)}}\right)\right]_t}{\left[\left(\frac{\overrightarrow{R_{mes}^{(2)}}}{R_{mes}^{(1)}}\right)\right]_0} - 1 \right] \qquad \text{Equation 2}$$

where $R_{mes}^{<i>}$ is the measured reflectance value at receiver i;

$$\left[\left(\frac{\overrightarrow{R_{mes}^{(2)}}}{R_{mes}^{(1)}}\right)\right]_t$$

is the ratio of the measured reflectance values at time t.

Optionally, the Equation 1 may take into account a factor for the effect of varying skin temperature, resulting in:

$$\Delta g = C_{cal} \cdot \text{Ratio}_{ref_t} + \text{Temp}_{corr} \cdot T_{drift} \qquad \text{Equation 3}$$

where $\text{Temp}_{corr}$ is correction factor accounting for the drift in skin temperature;

$T_{drift}$ is the difference in temperature between time t and time t=0.

Thus the relative glucose value g will be determined by:

$$g = g_{ref} + \Delta g \qquad \text{Equation 4}$$

At block 256, the algorithm propagates a probing light beam at a wavelength of 870 nm and measures two reflectance values, $R_{mes}^{<1>}$ and $R_{mes}^{<2>}$, at 2.1 mm and 6.9 mm distance, respectively, from the probing light beam 105. Optionally, at block 258, the algorithm measures the skin temperature of the user.

The algorithm then determines, at block 260, if a clinical state exists, e.g. in the case of a hypoglycaemia state, by verifying if the relative glucose value has gone below the critical glucose value ($g \leq g_c$), for example 5 mmol/L, or in the case of a hyperglycaemia state, by verifying if the estimated relative glucose value has gone above the critical glucose value ($g \geq g_c$), for example 11 mmol/L. In this specific example, values of $C_{cal}$=0.85 and $\text{Temp}_{corr}$=1.65 may be used in Equation 1 and Equation 3 for the purpose of computing the relative glucose value g. If a clinical state is determined then, at block 264, the algorithm generates an alarm and/or displays the determined clinical state. If not, the algorithm goes to block 262 where it verifies if a new reference glucose value is available, if yes it proceeds to block 252 where the new reference glucose value is inputted, if not, it then proceeds back to block 256 for the next iteration.

It is to be understood that other wavelengths, advantageously wavelengths between 500 nm and 1000 nm, a plurality of wavelengths and a plurality of receivers, with their associated receiver distances and reflectance values, may be used, along with appropriate values of $C_{cal}$ and $\text{Temp}_{corr}$.

Figure 4:
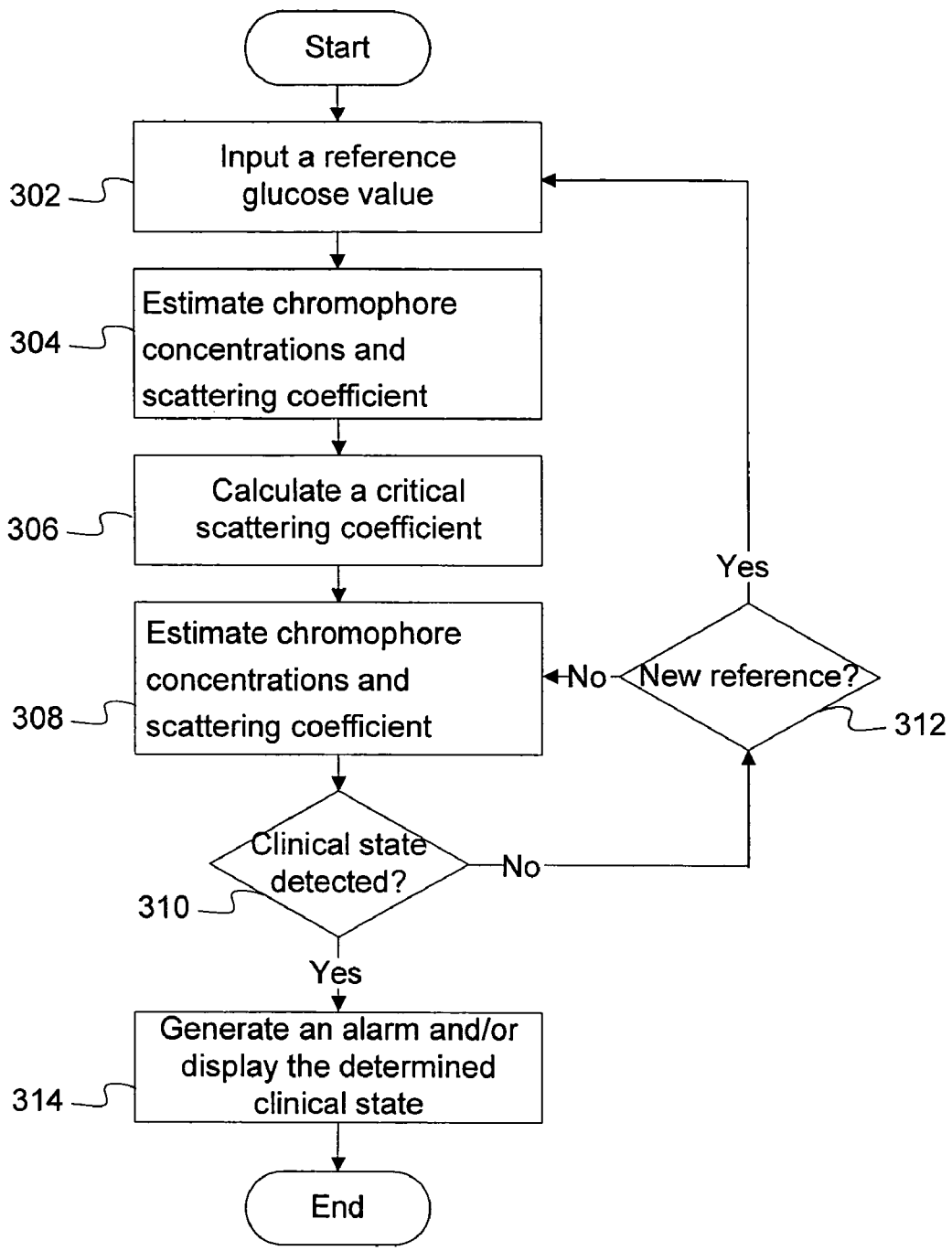
FIG. 4 is a flow diagram of a second example of a specific embodiment of the algorithm illustrated in FIG. 2.

A second example of a specific embodiment of the general monitoring and detection algorithm illustrated in FIG. 2 is depicted by the flow chart shown in FIG. 4. The steps composing the algorithm are indicated by blocks 302 to 314.

At block 302, the algorithm starts by receiving, as an input, a reference glucose value $g_{ref}$ provided by, for example, a reference meter such as a conventional blood-glucose monitor. Then, at block 304, the scattering coefficient is estimated (an example of a method for the estimation of the scattering coefficient will be further described below), the algorithm estimates the relative scattering coefficient $\delta_{\mu'sref}$ associated with the reference glucose value $g_{ref}$ and, at block 306, calculates a critical scattering coefficient using a predetermined relation between the scattering coefficient, the reference glucose value $g_{ref}$ and a critical glucose value. For example, the predetermined relation may be:

$$\delta_{\mu'sc} = +0.3\% \cdot (g_{ref} - g_c) + \delta_{\mu'sref} \qquad \text{Equation 5}$$

where $\delta_{\mu'sc}$ is the critical scattering coefficient; and $g_c$ is the critical glucose value, for example 5 mmol/L.

At block 308 the algorithm estimates the scattering coefficient and then determines, at block 310, if a clinical state exists, e.g. in the case of a hypoglycaemia state, by verifying if the estimated scattering coefficient has gone below the critical scattering coefficient ($\delta_{\mu's} \leq \delta_{\mu'sc}$) or in the case of a hyperglycaemia state, by verifying if the estimated scattering coefficient has gone above the critical scattering coefficient ($\delta_{\mu's} \geq \delta_{\mu'sc}$). If a clinical state is determined then, at block 314, the algorithm generates an alarm and/or displays the determined clinical state. If not, the algorithm goes to block 312 where it verifies if a new reference glucose value is available, if yes it proceeds to block 302 where the new reference glucose value is inputted, if not, it then proceeds back to block 308 for the next iteration.

Figure 5:
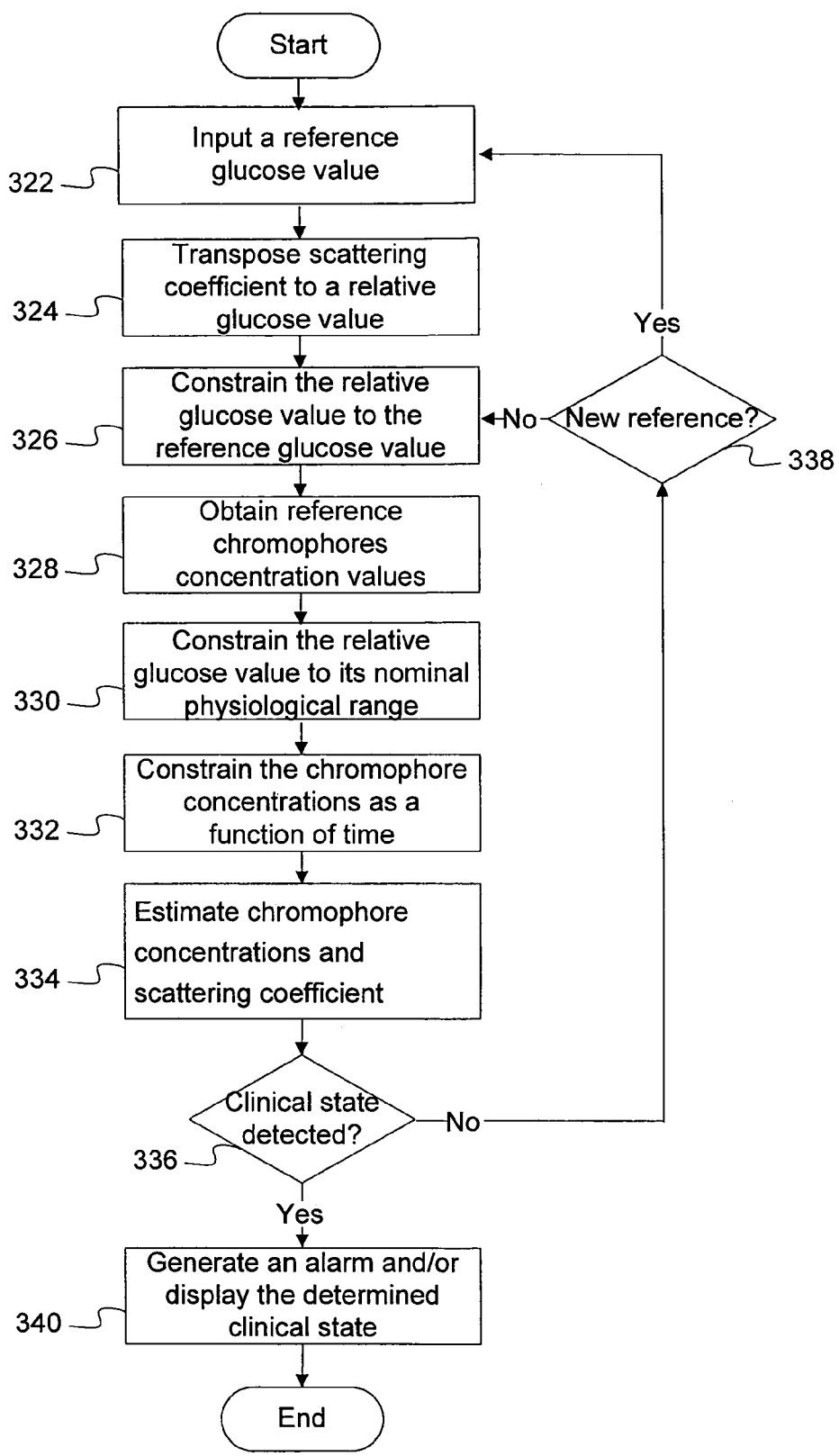
FIG. 5 is a flow diagram of a third example of a specific embodiment of the algorithm illustrated in FIG. 2.

A third embodiment of an algorithm for the detection of a clinical state is depicted by the flow chart shown in FIG. 5. The steps composing the algorithm are indicated by blocks 322 to 340.

At block 322, the algorithm starts by receiving, as an input, a reference glucose value $g_{ref}$ provided by, for example, a reference meter such as a conventional blood-glucose monitor. Then, at block 324, the algorithm transposes the scattering coefficient $\delta\mu'_s$ into a relative glucose value using a predetermined relation, for example:

$$\delta\mu'_s = -0.3\% \cdot g \qquad \text{Equation 6}$$

where
g is the relative glucose value.

At block 326, the relative glucose value is constrained to the reference glucose value obtained at block 322, e.g. $g=g_{ref}$, and, at block 326, the reference chromophore concentration values associated with the reference glucose value, $w_{ref}, b_{ref}, S_{ref}$, are estimated (an example of a method for the estimation of the chromophore concentration will be further described below) taking into account the constraint of block 326.

At block 330, the relative glucose value is constrained to its nominal physiological range, for example:

$$2 \text{ mmol/L} \leq g \leq 20 \text{ mmol/L}. \qquad \text{Equation 7}$$

At block 332, the chromophore concentrations are constrained to their respective reference chromophore concentrations, obtained at block 328, plus a tolerance which varies as a function of the elapsed time since the last reference glucose value was inputted. For example, the following constraints may be used:

$$w_{ref} - 1\%/\text{hr} \cdot t \leq w \leq w_{ref} + 1\%/\text{hr} \cdot t; \qquad \text{Equation 8}$$

$$b_{ref} - 0.01\%/\text{hr} \cdot t \leq b \leq b_{ref} + 0.01\%/\text{hr} \cdot t; \qquad \text{Equation 9}$$

$$S_{ref} - 1\%/\text{hr} \cdot t \leq S \leq S_{ref} + 1\%/\text{hr} \cdot t; \qquad \text{Equation 10}$$

where
t is the elapsed time since the last reference glucose value input.

Then, at block 334, estimates of the chromophore concentrations and scattering coefficient are estimated (an example of a method for the estimation of the chromophore concentration and scattering coefficient will be further described below), taking into account the constraints of blocks 330 and 332 represented by Equations 7, 8, 9 and 10, are used to estimate the relative glucose value g using Equation 6.

The algorithm then determines, at block 336, if a clinical state exists, e.g. in the case of a hypoglycaemia state, by verifying if the estimated relative glucose value has gone below the critical glucose value ($g \leq g_c$), for example 5 mmol/L, or in the case of a hyperglycaemia state, by verifying if the estimated relative glucose value has gone above the critical glucose value ($g \geq g_c$), for example 11 mmol/L. If a clinical state is determined then, at block 340, the algorithm generates an alarm and/or displays the determined clinical state. If not, the algorithm goes to block 338 where it verifies if a new reference glucose value is available, if yes it proceeds to block 322 where the new reference glucose value is inputted, if not, it then proceeds back to block 326 for the next iteration.

Figure 6:
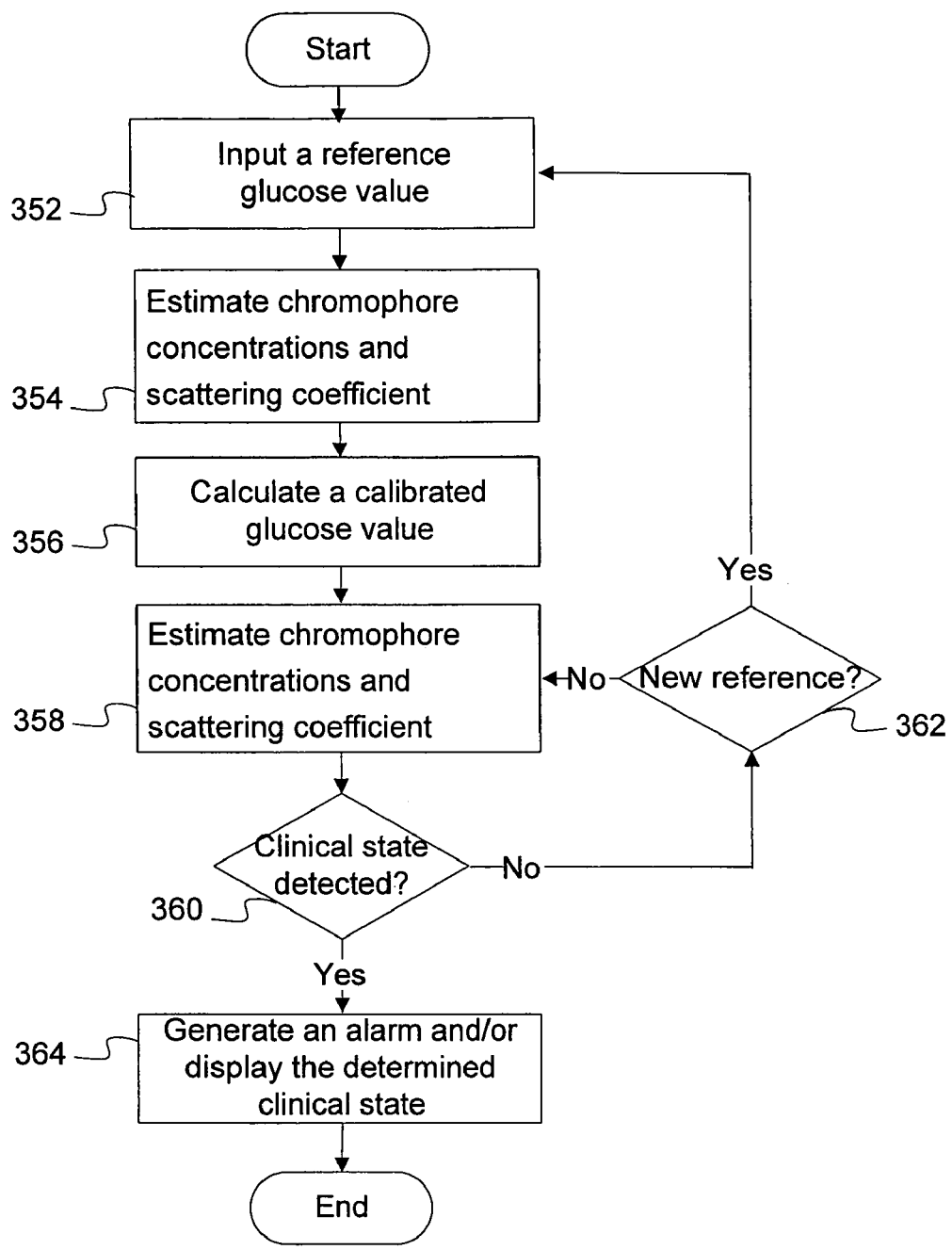
FIG. 6 is a flow diagram of a fourth example of a specific embodiment of the algorithm illustrated in FIG. 2.

A fourth embodiment of an algorithm for the detection of a clinical state is depicted by the flow chart shown in FIG. 6. The steps composing the algorithm are indicated by the blocks 352 to 364.

At block 352, the algorithm starts by receiving, as an input, a reference glucose value $g_{ref}$ provided by, for example, a reference meter such as a conventional blood-glucose monitor. Then, at block 354, using estimates of chromophore concentrations and of the scattering coefficient (an example of a method for the estimation of the chromophore concentration and scattering coefficient will be further described below), the algorithm estimates the relative scattering coefficient $\delta_{\mu'sref}$ associated with the reference glucose value $g_{ref}$ and, at block 356, it calculates the coefficients of a dynamic calibration relation between the last two measured reference glucose values and their associated scattering coefficients. For example, the following dynamic calibration relation may be used:

$$g = g_{refi} + (\delta_{\mu's} - \delta_{\mu'srefi}) \cdot (g_{refi} - g_{refi-1}) / (\delta_{\mu'srefi} - \delta_{\mu'srefi-1}). \qquad \text{Equation 11}$$

At block 358, using estimates of chromophore concentrations and of the scattering coefficient (an example of a method for the estimation of the chromophore concentration and scattering coefficient will be further described below), the algorithm estimates the relative scattering coefficient $\delta_{\mu's}$.

The algorithm then determines, at block 360, if a clinical state exists, e.g. in the case of a hypoglycaemia state, by verifying if the estimated relative glucose value has gone below the critical glucose value ($g \leq g_c$), for example 5 mmol/L, or in the case of a hyperglycaemia state, by verifying if the estimated relative glucose value has gone above the critical glucose value ($g \geq g_c$), for example 11 mmol/L, using Equation 16 to transpose the estimated scattering coefficient $\delta_{\mu's}$ into a glucose value g. If a clinical state is determined then, at block 364, the algorithm generates an alarm and/or displays the determined clinical state. If not, the algorithm goes to block 362 where it verifies if a new reference glucose value is available, if yes it proceeds to block 352 where the new reference glucose value is inputted, if not, it then proceeds back to block 358 for the next iteration.

Of course, other similar relationships between non-invasive physical measurements, a reference glucose value and a critical glucose value may be used to detect a hypoglycaemia or hyperglycaemia state.

Estimation of Chromophore Concentrations and Scattering Coefficient

Figure 7:
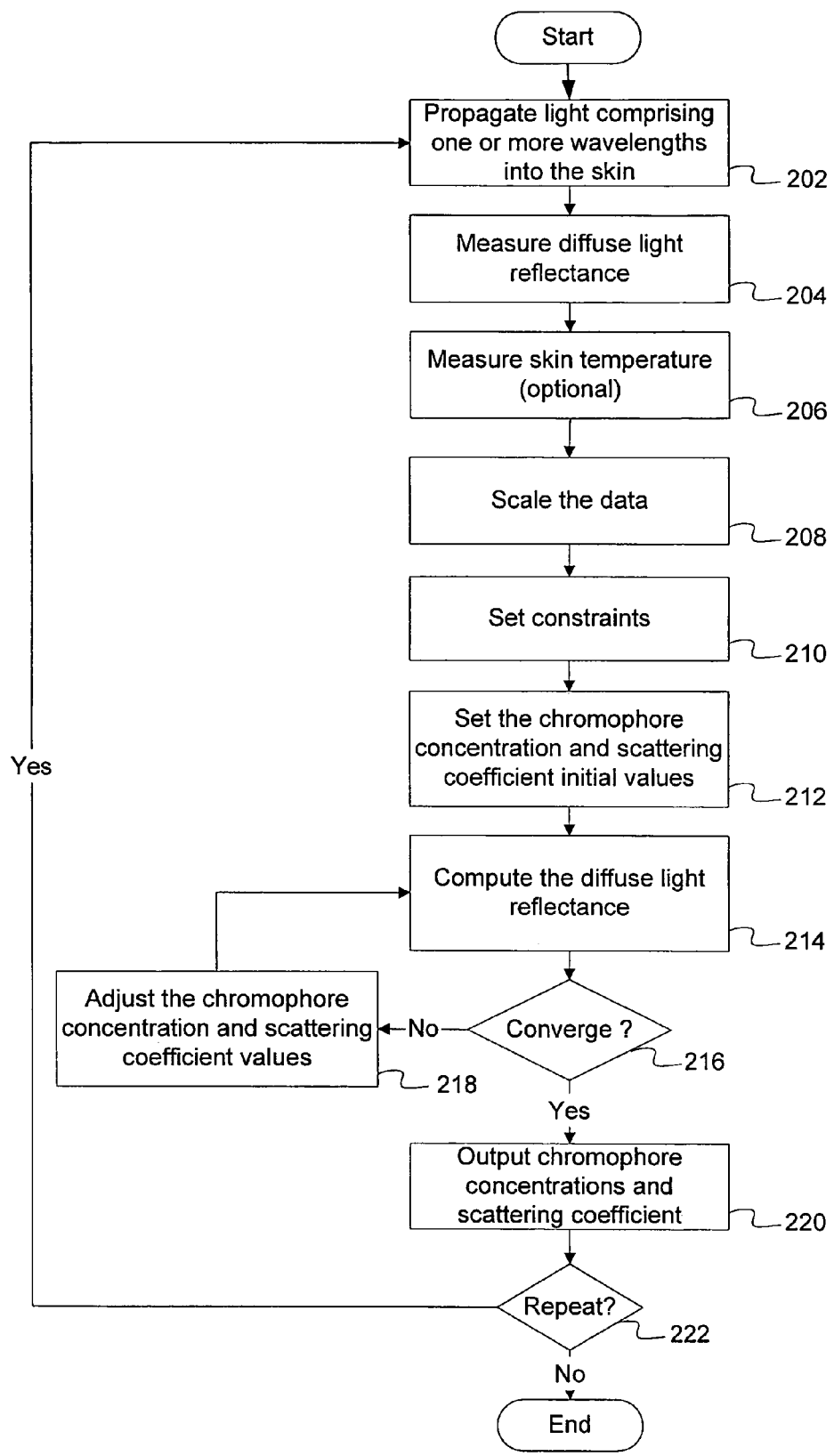
FIG. 7 is a flow diagram of an algorithm for the estimation of chromophore concentrations and scattering coefficient.

An algorithm that may be used for the estimation of chromophore concentrations and scattering coefficient is depicted by the flow chart shown in FIG. 7. The steps composing the algorithm are indicated by blocks 202 to 222.

At block 202, the algorithm starts by propagating probing light beam comprising two or more wavelengths into the skin, the wavelengths being selected according to the chromophores of interest such that variations in the concentrations of the various chromophores induce noticeable variations on light reflectance values at the input of the receiver collimating optics 114. The number of selected wavelengths should be such that there is at least one more wavelength than there are variables, i.e. number of chromophores of interest plus, if present, the scattering coefficient, ensuring that the ensuing model comprises a number of equations greater than the number of variables.

At block 204, the diffuse light reflectance is measured at two or more locations that are at different distances from the propagation point of the probing light beam of block 202. The diffuse light reflectance measurements are preferably taken simultaneously for all locations, the longer the time interval between each measurement, the less precise the algorithm results may become. The distances, as well as their values, are selected according to the chromophores of interest and the application. The more locations are used, the more precise the diffuse light reflectance model becomes, but also the more computation intensive is becomes and more expensive becomes the associated estimation apparatus 100.

At block 206, optionally, the skin temperature is measured.

At block 208, the algorithm scales the measured data provided to micro-controller 122 by the ADC 118. for example using the value measured at the light source monitor 108 or the signal at the first receiver $I_1$, so that the algorithm may be executed independently of the characteristics of the physical components used in the estimation apparatus 100 as well as power levels of the various light sources 102.

At block 210, fixed or dynamic constraints associated with each of the chromophores of interest, as well as with the scattering coefficient, are set. The constraints define a range of possible values for each of the chromophore concentrations, as well as the scattering coefficient, so as to prevent the algorithm from considering obviously erroneous values. In the case of dynamic constraints, the range of possible values for each of the chromophore concentrations and scattering coefficient takes the form of confidence interval whose center value is the last value of that chromophore concentration or of the scattering coefficient. The confidence interval is selected according to the maximum possible variation of each of the chromophore concentrations of interest, or of the scattering coefficient, in the time in between each execution of the algorithm.

Then, at block 212, the algorithm sets initial values for the chromophore concentrations and scattering coefficient, these values may be previously computed values, user inputted values, predefined or random values within the range of possible values defined by the constraints set at block 210.

The algorithm then computes, at block 214, the diffuse light reflectance for each of the receiver collimating optics 114, for each of the N wavelengths, as a function of the chromophore concentrations, the scattering coefficient and, optionally, the skin temperature obtained from temperature sensor 120, using a mathematical model of the diffuse light reflectance, which will be further explained in an example below.

At block 216, the algorithm verifies the convergence of the diffuse light reflectance values obtained at block 214 with the scaled measured data from block 208. If there is convergence, the algorithm proceeds to block 220, if not, it goes to block 218 where the chromophore concentrations and the scattering coefficient values are adjusted so as to minimize the error between the model values and the measured values using, for example, a curve fitting algorithm or any other suitable numerical optimization method. The algorithm then goes back to block 214 to compute a new set of diffuse light reflectance values using the adjusted chromophore concentrations and scattering coefficient values.

At block 220, once the diffuse light reflectance values have converged towards the measured values, the current chromophore concentrations and scattering coefficient values are outputted. Then, at block 222, the whole algorithm is repeated if continuous monitoring is desired, otherwise the algorithm ends.

Example

In a sample application, the chromophores of interest are water, oxyhemoglobin (HbO2) and deoxyhemoglobin (Hb). The light attenuation coefficients in the dermis associated with these chromophores, for various wavelengths, are well known in the literature, such as, for example, in Jacques; *Skin Optics Summary, Oregon Medical Laser Center News:* (January 1998). As well, the light attenuation coefficient has an intrinsic value associated with the dermis itself which is also well known.

The following wavelengths provide noticeable variations in light reflectance values in relation to variations in the water, HbO2 and Hb concentrations:

$$\lambda = (505\ 660\ 805\ 870\ 950)^T\ \text{nm}$$

The light attenuation coefficients for each chromophore may be represented by the vectors $\mu_{a.raw.\lambda}$:

$$\begin{pmatrix} \text{"Intrinsic"} \\ \text{"Water"} \\ \text{"HbO2"} \\ \text{"Hb"} \end{pmatrix} \quad \mu_{a.raw.505nm} = \begin{pmatrix} 0.669 \\ 0.025 \\ 110 \\ 110 \end{pmatrix} \text{cm}^{-1}$$

$$\mu_{a.raw.660nm} = \begin{pmatrix} 0.285 \\ 0.14 \\ 1.4 \\ 20 \end{pmatrix} \text{cm}^{-1} \quad \mu_{a.raw.805nm} = \begin{pmatrix} 0.249 \\ 0.95 \\ 5 \\ 5 \end{pmatrix} \text{cm}^{-1}$$

$$\mu_{a.raw.870nm} = \begin{pmatrix} 0.246 \\ 2.1 \\ 7.2 \\ 5 \end{pmatrix} \text{cm}^{-1} \quad \mu_{a.raw.950nm} = \begin{pmatrix} 0.245 \\ 12.5 \\ 8 \\ 4.3 \end{pmatrix} \text{cm}^{-1}$$

The reduced scattering coefficients in the dermis associated with these chromophores, for various wavelengths, are also well known in the literature.

The light scattering coefficients of the dermis may be represented as a function of wavelength by the following equation:

$$\mu'_{s.dermis}(\lambda) = \left[ 2 \cdot 10^5 \cdot \left(\frac{\lambda}{\text{nm}}\right)^{-1.5} + 2 \cdot 10^{12} \cdot \left(\frac{\lambda}{\text{nm}}\right)^{-4} \right] \text{cm}^{-1} \quad \text{Equation 12}$$

Which, for the selected wavelengths, results in the following values:

$\mu'_{s.dermis.505\ nm} = 48.4$ cm$^{-1}$ $\mu'_{s.dermis.660\ nm} = 22.3$ cm$^{-1}$
$\mu'_{s.dermis.805\ nm} = 13.5$ cm$^{-1}$ $\mu'_{s.dermis.870\ nm} = 11.3$ cm$^{-1}$
$\mu'_{s.dermis.950\ nm} = 9.29$ cm$^{-1}$ The compounded attenuation coefficients in the dermis for the selected chromophores may be modelized as a function of water (w), blood (b) and oxygen saturation (S). Blood (b) and oxygen saturation (S) are more convenient variables used to quantify oxyhemoglobin (HbO2) and deoxyhemoglobin (Hb).

Oxyhemoglobin (HbO2) may be approximated by:

$$\text{HbO2} \sim S*b; \quad \text{Equation 13}$$

and

Deoxyhemoglobin (Hb) by:

$$\text{Hb} \sim (1-S)*b \quad \text{Equation 14}$$

Thus, $\mu_{a.raw.\lambda}$ may be converted using the following transformation:

$$\mu_a(w, b, S) = \mu_{a.raw} \times \begin{bmatrix} (1-b) \cdot (1-w) \\ (1-b) \cdot w \\ b \cdot S \\ b \cdot (1-S) \end{bmatrix} \begin{pmatrix} \text{"Intrinsic"} \\ \text{"Water"} \\ \text{"HbO2"} \\ \text{"Hb"} \end{pmatrix}$$

The reduced scattering coefficient in the dermis may be further modelized for variations due to temperature and scattering coefficient changes related to glucose and other interfering analytes.

Assuming a measured skin temperature nominal value of T=34.5° C., the variation in scattering coefficient due to temperature changes may be expressed as:

$$\mu'_s(\delta\mu_s, T) = [1 + \delta T \mu'_s \cdot (T - 34.5)] \cdot (1 + \delta\mu'_s) \quad \text{Equation 15}$$

where $\delta T\mu'_s = -0.4\%$ is the nominal change in scattering coefficient due temperature; and $\delta\mu'_s$ is the scattering coefficient change.

The change of scattering due to glucose may be roughly approximated to $-0.3\%/\text{mmol/L}$, and may be precisely determined using prior experimental tests and/or calibration. The change of scattering due to temperature may also be precisely determined with prior experimental tests and/or calibration, for example by varying the skin temperature and measuring the associated change in the scattering coefficient.

The diffuse reflectance in the dermis as a function of water, blood, oxygen saturation, temperature, scattering coefficient change and the distance from the light source to the receivers, for each wavelength may be defined as:

$$R = \frac{a'}{4\cdot\pi}\cdot\left[\left(\frac{1}{\mu'_t}\right)\left(\mu_{e\!f\!f}+\frac{1}{r_1}\right)\frac{e^{-\mu_{e\!f\!f}r_1}}{r_1^2} + \left(\frac{1}{\mu'_t}+2\cdot z_b\right)\left(\mu_{e\!f\!f}+\frac{1}{r_2}\right)\frac{e^{-\mu_{e\!f\!f}r_2}}{r_2^2}\right] \quad \text{Equation 16}$$

where $$a' = \frac{\mu'_s}{\mu_a+\mu'_s};$$

$$\mu_{e\!f\!f} = \sqrt{3\cdot\mu_a\cdot(\mu_a+\mu'_s)};$$

$$\mu'_t = \mu_a + \mu'_s;$$

$$D = \frac{1}{3\cdot(\mu_a+\mu'_s)};$$

$$A = 1;$$

$$z_b = 2\cdot A\cdot D;$$

$$z_0 = \frac{1}{\mu_t};$$

$$r_1 = \sqrt{z_0^2+\rho^2};$$

$$r_2 = \sqrt{(z_0+2\cdot z_b)^2+\rho^2}; \text{ and}$$

$\rho$ is the distance from the light source to receiver.

The above implemented diffuse reflectance is modelized using a diffusion theory model of spatially resolved, steady-state diffuse reflectance such as disclosed in Farrell et al.; *A diffusion theory model of spatially resolves, steady-state diffuse reflectance for the non-invasive determination of tissue optical properties in vivo, Med. Phys.* 19 (4): 879-888 (July/August 1992).

Referring back to the algorithm of FIG. 7, at block 210, the constraints associated with each of the chromophores may be set as:

$$0.50 < w < 0.60; \quad \text{Equation 17}$$

$$0.1 < b < 0.3; \quad \text{Equation 18}$$

$$0.55 < S < 0.65; \quad \text{Equation 19}$$

$$-4\% < \delta\mu'_s < 1\%. \quad \text{Equation 20}$$

Then, the initial values of block 212 may be set as:
w=0.55;
b=0.2;
S=0.65;
$\delta\mu'_s$=0%.

Thus, at block 214, the algorithm computes the diffuse light reflectance for every wavelength $\lambda$ and every receiver 114 using the model represented by Equation 5, varying the values of w, b, S and $\delta\mu'_s$ at block 218 so as to minimize the error between the measured data and the computed R for each distance $\rho$ and wavelength $\lambda$ at block 216, simultaneously.

It should be noted that oxyhemoglobin (HbO2) and deoxyhemoglobin (Hb) chromophore concentration values may be used to detect an ischemic state. More specifically, normal oxygen saturation (S), i.e. the ratio of oxyhemoglobin (HbO2) and deoxyhemoglobin (Hb), should be around 60%. An ischemic state may be detected when this ratio goes down to, for example, 40%.

Although the present invention has been described by way of particular embodiments and examples thereof, it should be noted that it will be apparent to persons skilled in the art that modifications may be applied to the above-described embodiments without departing from the scope of the present invention.

What is claimed is:

1. A method for detecting a clinical state in a subject, comprising:
   acquiring a reference value of blood-glucose of the subject;
   correlating one or more non-invasive physical measurements of the body of the subject with the reference value of blood-glucose of the subject;
   measuring the one or more non-invasive physical measurements of the body of the subject;
   computing an estimation parameter value representative of a variation in glucose value using the measured one or more non-invasive physical measurements and the correlation between the one or more non-invasive physical measurements of the body of the subject with the reference value of blood-glucose of the subject;
   comparing the estimation parameter value with a critical parameter value, wherein the critical parameter value is indicative of a clinical state; and
   indicating that a clinical state is detected if the estimation parameter value has reached the critical parameter value.

2. A method according to claim 1, wherein if a clinical state is not detected, the method returns to measuring the one or more non-invasive physical measurements of the body of the subject.

3. A method according to claim 1, wherein before returning to measuring the one or more non-invasive physical measurements of the body of the subject, the method verifies if a new reference value of blood-glucose of the subject is available, if so the method returns to acquiring a reference value of blood-glucose of the subject.

4. A method for detecting a clinical state in a subject, comprising:
   acquiring a reference value of blood-glucose of the subject;
   correlating the reflectance of light in the skin with the reference value of blood-glucose of the subject;
   propagating at least one probing light beam into the skin of the subject from a propagation point;
   measuring reflectance values of the at least one probing light beam from at least two distances from the propagation point;
   computing an estimation parameter value representative of a variation in glucose value using the measured reflectance values and the correlation between the reflectance of light in the skin with the reference value of blood-glucose of the subject;

comparing the estimation parameter value with a critical parameter value, wherein the critical parameter value is indicative of a clinical state; and indicating that a clinical state is detected if the estimation parameter value has reached the critical parameter value.

5. A method according to claim 4, wherein the blood-glucose value of the subject is acquired from a conventional blood-glucose monitor.

6. A method according to claim 4, wherein the clinical state is one of a hypoglycemic state and hyperglycemic state.

7. A method according to claim 4, wherein the at least one probing light beam has a wavelength between 500 nm and 1000 nm.

8. A method according to claim 4, wherein the correlation between the reflectance of light in the skin of the subject with the reference value of blood-glucose of the subject includes a reflectance mathematical model.

9. A method according to claim 4, wherein the correlation between the reflectance of light in the skin of the subject with the reference value of blood-glucose of the subject includes a chromophore concentration estimation mathematical model.

10. A method according to claim 4, wherein the correlation between the reflectance of light in the skin of the subject with the reference value of blood-glucose of the subject includes a scattering coefficient estimation mathematical model.

11. A method according to claim 4, further comprising measuring a temperature of the skin of the subject and wherein the correlation between the reflectance of light in the skin of the subject with the reference value of blood-glucose of the subject includes a skin temperature correction factor.

12. A method for detecting a clinical state in a subject, comprising:
acquiring a reference value of blood-glucose of the subject;
correlating at least two parameters of skin of the body of the subject with the reference value of blood-glucose of the subject;
propagating at least two probing light beams into the skin from at least one propagation point;
measuring reflectance values of the at least two probing light beams from at least two distances from the at least one propagation point;
estimating values representative of the at least two parameters of skin of the body of the subject using the measured reflectance values and a mathematical skin parameter estimation model;
computing an estimation parameter value representative of a variation in glucose value using the estimated values of the at least two parameters of skin of the body of the subject and the correlation between the at least two parameters of skin of the body of the subject with the reference value of blood-glucose of the subject;
comparing the estimation parameter value with a critical parameter value, wherein the critical parameter value is indicative of a clinical state; and
indicating that a clinical state is detected if the estimation parameter value has reached the critical parameter value.

13. A method according to claim 12, wherein if a clinical state is not detected the method returns to measuring reflectance values of the at least two probing light beams from at least two distances from the at least one propagation point.

14. A method according to claim 12, wherein before returning to measuring reflectance values of the at least two probing light beams from at least two distances from the at least one propagation point, the method verifies if a new reference value of blood-glucose of the subject is available, if so the method returns to acquiring a reference value of blood-glucose of the subject.

15. A method according to claim 12, wherein the at least two parameters of skin of the body of the subject is selected from a group including chromophore concentrations, a scattering coefficient and the temperature of the skin.

16. A method according to claim 12, wherein the blood-glucose value of the subject is obtained from a conventional blood-glucose monitor.

17. A method according to claim 12, wherein the clinical state is one of a hypoglycemic state and a hyperglycemic state.

18. A method according to claim 12, wherein the at least one probing light beam has a wavelength between 500 nm and 1000 nm.

19. A method according to claim 12, further comprising measuring a temperature of the skin of the subject and wherein the mathematical skin parameter estimation model includes a skin temperature correction factor.

20. A method for computing an estimate of a value representative of at least one parameter of skin selected from a group including chromophore concentrations and a scattering coefficient, comprising:
propagating at least two probing light beams into the skin from at least one propagation point;
measuring reflectance values of the at least two probing light beams from at least two distances from the at least one propagation point;
computing estimates of the at least one parameter of skin of the body of the subject using a reflectance mathematical model; and
outputting the estimate of the value representative of the at least one selected parameters of skin.

21. A method according to claim 20, wherein the at least one parameter of skin includes oxyhemoglobin (HbO2) and deoxyhemoglobin (Hb) chromophore concentrations and further comprising:
comparing the estimates of a ratio of oxyhemoglobin (HbO2) and deoxyhemoglobin (Hb) chromophore concentrations with a critical parameter value, wherein the critical parameter value is indicative of an ischemic state; and
indicating that a clinical state is detected if the estimation parameter value has reached the critical parameter value.

22. A method according to claim 21, wherein if an ischemic state is not detected the method returns to propagating at least two probing light beams into the skin from at least one propagation point.

23. A method according to claim 20, further comprising measuring a temperature of the skin of the subject and wherein the reflectance mathematical model includes a skin temperature correction factor.

24. An apparatus for detecting a clinical state in a subject, comprising:
an input for acquiring a reference value of blood-glucose of the subject;
a measurement mechanism for measuring one or more non-invasive physical measurements of the body of the subject;
a display;
a microcontroller in operatively connected to the input, the measurement mechanism and the display, wherein the microcontroller comprises an algorithm for:
computing an estimation parameter value representative of a variation in glucose value using the measured one or more non-invasive physical measurements and a correlation between the one or more non-invasive physical measurements of the body of the subject with the reference value of blood-glucose of the subject;

comparing the estimation parameter value with a critical parameter value, wherein the critical parameter value is indicative of a clinical state; and indicating on the display that a clinical state has been detected if the estimation parameter value has reached the critical parameter value.

25. An apparatus according to claim 24, wherein the one or more non-invasive physical measurements of the body of the subject is the reflectance of light in the skin of the subject and wherein the measurement mechanism includes:

an emitter for propagating at least one probing light beam into the skin of the subject from a propagation point; and a receiver for measuring reflectance values of the at least one probing light beam from at least two distances from the propagation point.

26. An apparatus according to claim 25, wherein the at least one probing light beam has a wavelength between 500 nm and 1000 nm.

27. An apparatus according to claim 25, further comprising a temperature sensor for measuring the temperature of the skin of the subject and wherein the computing of the estimation parameter value representative of a variation in glucose value includes a skin temperature correction factor.

28. An apparatus for computing an estimate of a value representative of at least one parameter of skin selected from a group including chromophore concentrations and a scattering coefficient, comprising:

emitter for propagating at least two probing light beams into the skin from at least one propagation point;

at least two receivers for measuring reflectance values of the at least two probing light beams from at least two distances from the at least one propagation point;

a display;

a microcontroller in operatively connected to the receivers and the display, wherein the microcontroller comprises an algorithm for:

computing estimates of the at least one parameter of skin of the body of the subject using a reflectance mathematical model; and outputting to the display the estimate of the value representative of the at least one selected parameters of skin.

29. An apparatus according to claim 28, further comprising a temperature sensor for measuring the temperature of the skin of the subject and wherein the reflectance mathematical model includes a skin temperature correction factor.

30. An apparatus according to claim 28, wherein the at least one parameter of skin includes oxyhemoglobin (HbO2) and deoxyhemoglobin (Hb) chromophore concentrations and wherein the algorithm further comprises:

comparing the estimates of a ratio of oxyhemoglobin (HbO2) and deoxyhemoglobin (Hb) chromophore concentrations with a critical parameter value, wherein the critical parameter value is indicative of an ischemic state; and indicating on the display that a clinical state has been detected if the estimation parameter value has reached the critical parameter value.

* * * * *